(12) United States Patent
Sengun et al.

(10) Patent No.: US 11,666,431 B2
(45) Date of Patent: *Jun. 6, 2023

(54) OVERDRIVE PREVENTION FOR EXPANDABLE ANCHOR

(71) Applicant: Medos International Sàrl, Le Locle (CH)

(72) Inventors: Mehmet Z. Sengun, Canton, MA (US); Gregory R. Whittaker, Stoneham, MA (US)

(73) Assignee: Medos International Sarl, Le Locle (CH)

( * ) Notice: Subject to any disclaimer, the term of this patent is extended or adjusted under 35 U.S.C. 154(b) by 660 days.

This patent is subject to a terminal disclaimer.

(21) Appl. No.: 16/546,884

(22) Filed: Aug. 21, 2019

(65) Prior Publication Data

US 2019/0374331 A1 Dec. 12, 2019

Related U.S. Application Data

(63) Continuation of application No. 15/164,307, filed on May 25, 2016, now Pat. No. 10,390,936.

(51) Int. Cl.
*A61F 2/08* (2006.01)
*A61B 17/04* (2006.01)
*A61B 90/00* (2016.01)

(52) U.S. Cl.
CPC ........ *A61F 2/0811* (2013.01); *A61B 17/0401* (2013.01); *A61B 2017/0403* (2013.01);
(Continued)

(58) Field of Classification Search
CPC ............................ A61F 2/0811; A61B 17/0401
See application file for complete search history.

(56) References Cited

U.S. PATENT DOCUMENTS 2,604,912 A 7/1952 Walker
3,943,800 A 3/1976 Lesner
(Continued)

FOREIGN PATENT DOCUMENTS

CN 105559838 A 5/2016
EP 3020371 A2 5/2016
(Continued)

OTHER PUBLICATIONS

U.S. Appl. No. 15/164,307, filed May 25, 2016, Mehmet Z. Sengun et al.
(Continued)

*Primary Examiner* — Si Ming Ku

(57) ABSTRACT

Surgical devices and methods are provided for anchoring tissue to bone, and more particularly methods and devices are provided for preventing over-insertion of an expander into a sheath of a two-piece anchor. For example, a tendon anchoring system is provided with an anchor assembly and an inserter tool. The anchor assembly includes a sheath with a threaded lumen and a threaded expander screw configured to be threadably disposed within the sheath to cause the sheath to expand outward. The inserter tool includes an elongate outer shaft with a distal end configured to couple to a proximal end of the sheath, and an elongate inner shaft with a distal drive tip configured to engage a proximal end of the expander screw. In one embodiment, the inner shaft can be rotatable relative to the outer shaft to thread the expander screw into the sheath, and the inner shaft can be prevented from rotating relative to the outer shaft when the expander screw is fully threaded into the sheath to prevent over-insertion of the expander screw into the sheath.

14 Claims, 7 Drawing Sheets

(52) U.S. Cl.
CPC ............. *A61B 2017/0409* (2013.01); *A61B 2017/0412* (2013.01); *A61B 2017/0424* (2013.01); *A61B 2017/0425* (2013.01); *A61B 2017/0464* (2013.01); *A61B 2090/034* (2016.02); *A61B 2090/035* (2016.02); *A61F 2002/0835* (2013.01); *A61F 2002/0858* (2013.01); *A61F 2002/0888* (2013.01)

(56) References Cited

U.S. PATENT DOCUMENTS

| | | | |
|---|---|---|---|
| 5,101,698 A | 4/1992 | Paradiso | |
| 5,524,512 A | 6/1996 | Wolfe | |
| 5,682,800 A | 11/1997 | Jore | |
| 6,436,142 B1 | 8/2002 | Paes et al. | |
| 6,497,166 B1 | 12/2002 | Fleckenstein | |
| 6,558,097 B2 | 5/2003 | Mallet et al. | |
| 7,160,109 B2 | 1/2007 | Gervais et al. | |
| 7,787,934 B2* | 8/2010 | Mazzocchi | A61B 90/39 600/414 |
| 8,763,499 B2 | 7/2014 | Dahners | |
| 10,390,936 B2 | 8/2019 | Sengun et al. | |
| 2006/0079903 A1 | 4/2006 | Wong | |
| 2007/0038221 A1* | 2/2007 | Fine | A61F 2/0811 606/232 |
| 2008/0289459 A1 | 11/2008 | Yablon | |
| 2011/0112576 A1 | 5/2011 | Nguyen et al. | |
| 2012/0029577 A1 | 2/2012 | Kerr et al. | |
| 2012/0239095 A1 | 9/2012 | Barrall | |
| 2013/0125714 A1 | 5/2013 | Dahners | |
| 2013/0268010 A1 | 10/2013 | Santangelo et al. | |
| 2015/0190130 A1 | 7/2015 | Groh | |

FOREIGN PATENT DOCUMENTS

| | | |
|---|---|---|
| JP | 2011528270 A | 11/2011 |
| WO | 9417961 A1 | 8/1994 |
| WO | 2016057514 A1 | 4/2016 |

OTHER PUBLICATIONS

European Search Report for Application No. 17172946.0, dated Jan. 26, 2018 (10 Pages).

* cited by examiner

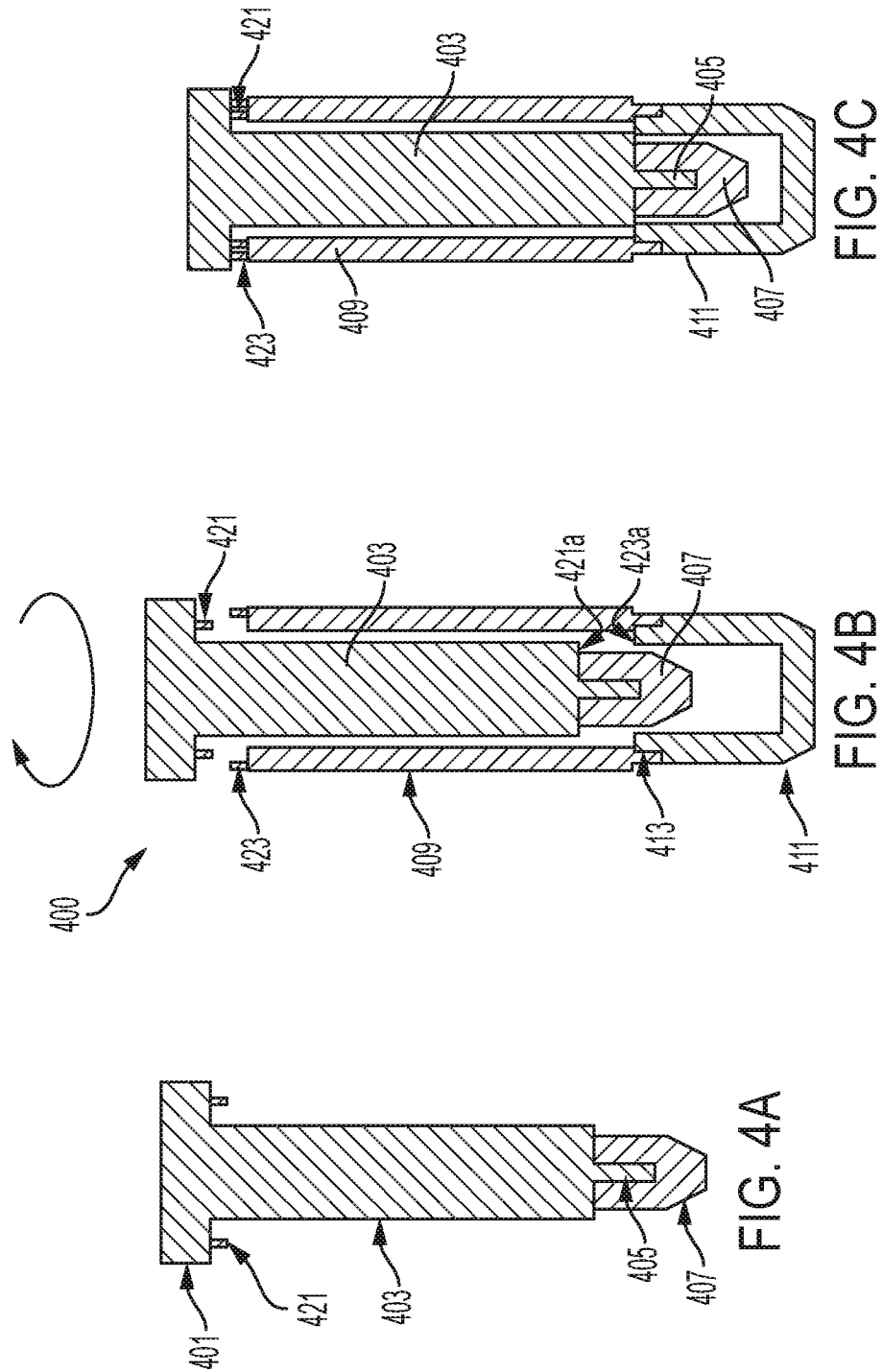

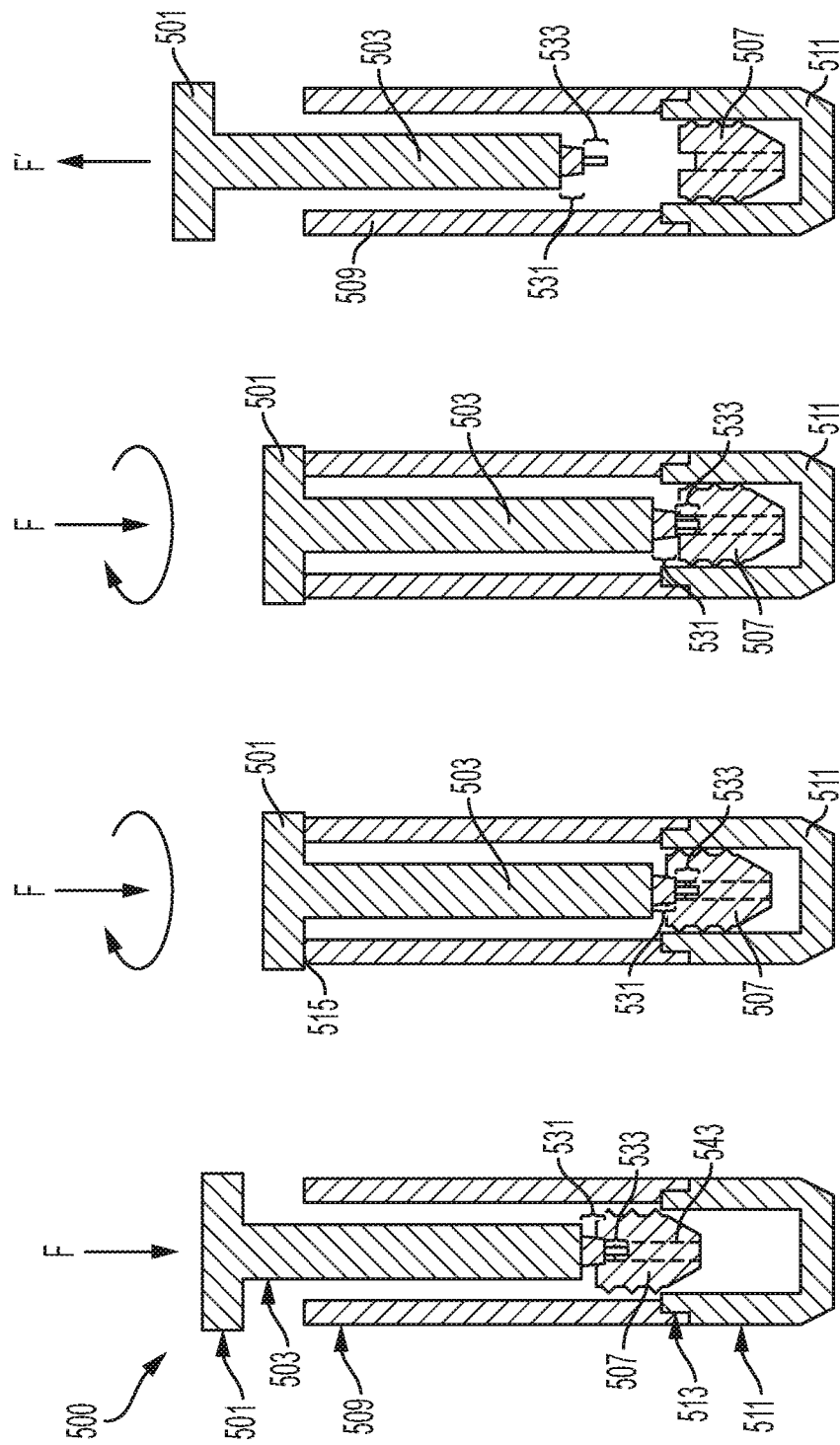

OVERDRIVE PREVENTION FOR EXPANDABLE ANCHOR

CROSS-REFERENCE TO RELATED APPLICATION

The present application is a continuation application of U.S. patent application Ser. No. 15/164,307, filed May 25, 2016, entitled "OVERDRIVE PREVENTION FOR EXPANDABLE ANCHOR," which is hereby incorporated herein by reference in its entirety.

FIELD

Surgical methods and devices are provided for anchoring tissue to bone, and more particularly methods and devices are provided for preventing over-insertion of an expander into a sheath of a two-piece anchor.

BACKGROUND

Disorders of the long head of the biceps tendon are a common source of shoulder pain and may occur in association with other diagnoses such as rotator cuff tears, superior labrum anterior posterior tears, impingement syndrome and capsular injuries, or may be present as an isolated source of shoulder pain. The treatment options for disorders of the long head of the biceps (LHB) continue to evolve and can include LHB tenodesis. In a tenodesis procedure, a suture is passed through the base of the LHB to locate the LHB in the subacromial space and to provide proximal control during the dissection. Once the suture is placed, the LHB is cut near the glenoid attachment. A sizer can be used to measure the tendon size and to thereby determine the appropriately sized bone screw. Once the screw is selected, a bone hole is drilled and a tendon fork is then used to push the tendon down into the bone hole. A bone screw is then delivered into the bone hole to anchor the tendon within the bone hole.

Some bone screws for anchoring a tendon include two pieces, namely a sheath and a screw that is inserted into the sheath and that causes the sheath to expand radially outward to anchor the sheath, and thereby the tendon, within the bone hole. While current two-piece anchors can be very effective, one drawback is that the screw can be over-inserted into the sheath. This can cause various undesirable effects, such as unwanted rotation of the sheath, movement of the sheath, and/or over-expansion and thus fracture of or damage to the sheath.

Accordingly, there remains a need for improved methods and devices for anchoring tissue to bone, and in particular for limiting an insertion depth of a screw into a sheath of a two-piece anchor device.

SUMMARY

Various implants, tools and methods are provided for attaching a tendon to bone.

In one aspect, a tendon anchoring system is provided that includes an anchor assembly and an inserter tool. The anchor assembly has a sheath with a threaded lumen formed therein, and a threaded expander screw that is configured to engage the threaded lumen in the sheath such that the expander screw causes the sheath to expand outward to engage a bone hole. The inserter tool has an elongate outer shaft and an elongate inner shaft. The elongate outer shaft has a distal end configured to couple to a proximal end of the sheath. The elongate inner shaft has a distal drive tip configured to engage a corresponding drive recess formed in a proximal end of the expander screw. In an exemplary embodiment, the inner shaft can be rotatable relative to the outer shaft to thread the expander screw into the sheath, and the inner shaft can be prevented from rotating relative to the outer shaft when the expander screw is fully threaded into the sheath to prevent over-insertion of the expander screw into the sheath.

The tendon anchoring system can vary in any number of ways. For example, the inner and outer shafts can include complementary abutting surfaces that are configured to contact one another. In one embodiment, a distal end of the elongate outer shaft can be configured to abut the proximal end of the sheath to prevent over-insertion of the expander screw into the sheath. In another example, the inner shaft can include a vertical stop surface formed on a distal end thereof that is configured to engage a corresponding vertical stop surface formed on the proximal end of the expander screw such that the vertical stop surfaces limit insertion of the distal drive tip into the drive recess. Additionally, the vertical stop surfaces can each have a height that is less than a thread pitch of the expander screw. In still another example, the inner shaft can have at least one engagement feature formed thereon and configured to engage a corresponding engagement feature formed on the outer shaft when the expander is fully threaded into the sheath such that the engagement features prevent further rotation of the inner shaft relative to the outer shaft. In one embodiment, the drive tip is non-threaded and has a shape that corresponds to a shape of the drive recess in the expander screw such that rotation of the drive tip causes a corresponding rotation of the expander screw. In another embodiment, the engagement feature on each of the inner shaft and the outer shaft comprises at least one tooth. The at least one tooth can be angled such that the teeth form a mechanical interlock when mated to prevent rotation of the inner shaft relative to the outer shaft.

In another aspect, a tendon anchoring system is provided that includes an anchor assembly having a sheath with a threaded lumen formed therein, and a threaded expander screw configured to threadably engage the threaded lumen in the sheath such that the expander screw causes the sheath to expand outward to engage a bone hole. The tendon anchoring system also includes an inserter tool having an elongate outer shaft and elongate inner shaft. The elongate outer shaft has proximal and distal ends and an inner lumen extending therethrough. The distal end is configured to couple to a proximal end of the sheath. The elongate inner shaft of the inserter tool has a distal drive tip with a drive portion configured to disengage from the drive recess when the expander screw is fully threaded into the sheath.

In one embodiment, the drive portion has a flat head having opposed planer surfaces, and the drive recess comprises an elongate slot formed in a proximal end of the expander screw. In another embodiment, the distal drive tip can include a pin extending distally from the drive portion. The pin can be configured to extend into a lumen formed in the expander screw and it can be freely rotatable relative to the expander screw. In still another embodiment, the inner shaft includes a handle coupled to a proximal end thereof and configured to abut against a proximal end of the outer shaft when the expander screw is fully threaded into the sheath. Additionally, the proximal drive portion can be configured to disengage from the drive recess when the handle on the inner shaft abuts against the proximal end of the outer shaft.

Methods for implanting an anchor in bone are also provided. In one embodiment, the method includes rotating an inner shaft of an inserter tool relative to an outer shaft of the inserter tool to rotatably drive a threaded expander screw distally into a threaded inner lumen of a sheath coupled to the outer shaft and disposed within a bone hole. The expander screw causes the sheath to expand radially outward to engage bone. The distal advancement of the expander screw into the sheath is limited to a predetermined insertion depth such that over-insertion of the expander screw into the sheath is prevented.

The method can vary in any number of ways. For example, the inner shaft can be prevented from rotating relative to the outer shaft when a threaded distal drive tip on the inner shaft is fully threaded into a threaded bore in the expander screw. As another example, a distal end of the inner shaft can abut a proximal end of the sheath when the expander screw reaches the predetermined insertion depth. In another example, the inner shaft can include a vertical stop surface formed on a distal end thereof that engages a corresponding vertical stop surface formed on a proximal end of the expander screw when the expander screw reaches the predetermined insertion depth. In one embodiment, at least one engagement feature formed on the inner shaft can engage a corresponding engagement feature formed on the outer shaft when the expander screw reaches the predetermined insertion depth. In still another example, a distal drive tip of the inner shaft disengages from a drive recess in the expander screw when the expander screw reaches the predetermined insertion depth.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 4A is a side cross-sectional view of another embodiment of an inner shaft and expander screw of a tendon anchoring assembly;

FIG. 4B is a side cross-sectional view of the inner shaft and expander screw of FIG. 4A being advanced through an outer shaft and into a sheath coupled to the outer shaft;

FIG. 4C is a side cross-sectional view of the tendon anchoring assembly of FIG. 4B, showing the screw fully inserted into the sheath;

FIG. 5E is a side cross-sectional view of the inner shaft of FIG. 5A coupled to the expander screw of FIG. 5C, with both components being advanced through an outer shaft and into a sheath;

FIG. 5F is a side cross-sectional view of the tendon anchoring assembly of FIG. 5E, showing the expander screw advanced into the sheath;

FIG. 5G is a side cross-sectional view of the tendon anchoring system of FIG. 5F, showing a drive feature on a distal end of the inner shaft disengaged from the expander screw; and FIG. 5H is a side cross-sectional view showing the inner shaft of FIG. 5G being removed from the expander screw.

DETAILED DESCRIPTION

Figure 1A:
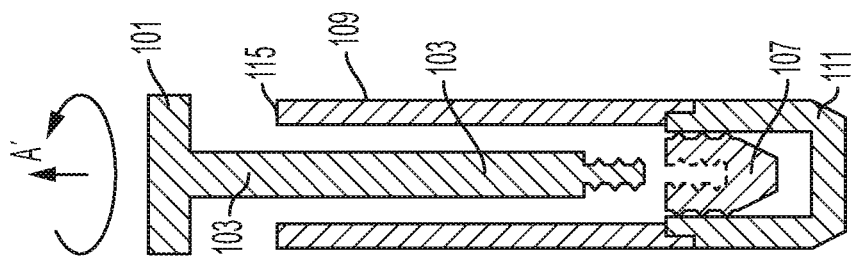
FIG. 1A is a side cross-sectional view of an inner shaft and expander screw of a tendon anchoring assembly according to one embodiment of the invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In general, methods and devices are provided for anchoring a ligament or tendon to bone. In an exemplary embodiment, the methods and devices are used to perform a biceps tenodesis surgery, however, a person skilled in the art will appreciate that the devices and methods can be used in various procedures and for anchoring any tissue to bone. In exemplary embodiments, various inserter tools are provided for delivering various bone anchors including an expandable sheath and an expander into a bone hole to anchor a tendon or other tissue within the bone hole. The inserter tools are configured to drive the expander into the sheath to a desired depth without over-insertion of the expander into the sheath. Over-driving the expander into the sheath may cause damage or breakage of the sheath, expander, ligament or tendon, and/or bone. Under-driving the expander into the sheath may cause an insecure anchoring of the ligament or tendon to the bone, which may lead to subsequent damage or breakage. Current inserter tool drivers can still rotate and cause the expander to continue to rotate and pull the sheath proximally or damage the sheath.

Accordingly, methods and devices for anchoring a ligament or tendon to bone are provided in which over insertion of the expander into the sheath is prevented. The methods and devices include a system of any one or more of the following components: an anchor assembly having an expander screw and sheath, and an inserter tool having an outer shaft and an inner shaft having a distal drive tip.

FIGS. 1A-1D illustrate one embodiment of a tendon anchoring system 100 that includes an anchor assembly and an inserter tool. The anchor assembly has an expander screw 107 and a sheath 111. The inserter tool 100 has an inner shaft 103 configured to couple to the expander screw 107, and an outer shaft 109 disposed around the inner shaft 103 and configured to couple to the sheath 111. The inner shaft 103 of the sheath inserter tool 100 has a distal end having a distal tip 105 that is configured to mate to the threaded expander screw 107. In this embodiment, the outer shaft 109 is configured to limit distal advancement of the inner shaft 103 to thereby limit advancement of the expander screw 107 into the sheath 111, thus preventing the expander screw 107 from being over driven into the sheath 111.

The anchor assembly can have a variety of configurations, but in general the sheath 111 is configured to receive the expander screw 107 therein such that the expander screw 107 is effective to cause the sheath 111 to expand radially outward into bone to anchor a tendon disposed around the sheath within a bone hole. The sheath 111 can be formed from any bio-compatible or bio-absorbable material, and it can have various configurations. In the illustrated embodiment, the sheath 111 has a generally elongate cylindrical shape with a generally circular or ovular cross-sectional geometry. The sheath 111 can have a distal-most end with a concave shape (not shown) to help seat the tendon. The sheath 111 can also include bone-engaging surface features on an external surface thereof, such as threads or ribs form thereon and extending radially there around. In one exemplary embodiment, the ribs are uni-planar and do not form threads, as the sheath 111 is preferably not rotated during insertion into a bone hole.

As described above, the sheath 111 is configured to receive a screw therein that is effective to expand the sheath 111 to anchor the sheath and ligament disposed therearound within a bone hole. The expander screw 107 can also have a variety of configurations, but in general it has a generally cylindrical shape with a diameter that, along at least portions thereof, is greater than an inner diameter $S_2$ of the sheath 111. In an exemplary embodiment, the expander screw 107 has a constant minor diameter $E_1$ along at least a proximal portion, and preferably along a majority of the length. A distal portion of the screw 107 can taper distally inward to a reduced diameter $E_2$ at the distal-most end. The screw 107 can have threads formed on all or part of an external surface thereof to facilitate engagement with the sheath 111. In certain embodiments, the expander screw 107 can be fully cannulated for allowing it to be delivered to the sheath 111, and the screw 107 can have a flat proximal facing surface and a flat distal facing surface. The proximal and distal surfaces of the screw 107 can have various shapes and the shapes configured to conform to the sheath and/or the bone surface.

The sheath inserter tool 100 can also have a variety of configurations, but as indicated above includes inner and outer shafts 103, 109. The inner shaft 103 can have a general elongate configuration with a distal end that is configured to mate to the screw 107. For example, the distal end can include a drive tip 105 formed thereon for engaging the screw. In one embodiment, the drive tip 105 has a hexagonal configuration for extending into a hexagonal drive socket formed in the proximal end of the screw 107 to thereby allow the inner shaft 103 to rotate the screw 107. The proximal end of the inner shaft 103 can include a driver handle 101 formed thereon or coupled thereto for facilitating rotation of the inner shaft. The driver handle assembly 101 can have a variety of configurations, but as shown the handle 101 has a generally elongate configuration to facilitate grasping thereof. The handle 101 can also have a diameter $H_1$ (or a length) that is greater than an inner diameter $O_1$ of the outer shaft 109, such that it will abut a proximal end 115 of the outer shaft 109 of the inserter tool 100.

The outer shaft 109 of the inserter tool 100 can also have a variety of configurations. In an exemplary embodiment, the outer shaft 109 has a generally elongate hollow cylindrical configuration having an outer diameter $O_2$ such that a distal end of the outer shaft 109 mates to a proximal end 113 of the sheath 111 or at least abuts against it.

Figure 1B:
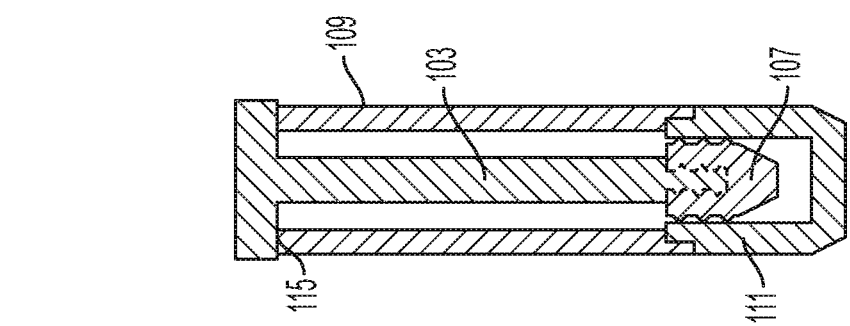
FIG. 1B is a side cross-sectional view of the inner shaft and expander screw of FIG. 1A being advanced through an outer shaft and into a sheath coupled to the outer shaft.
Figure 1C:
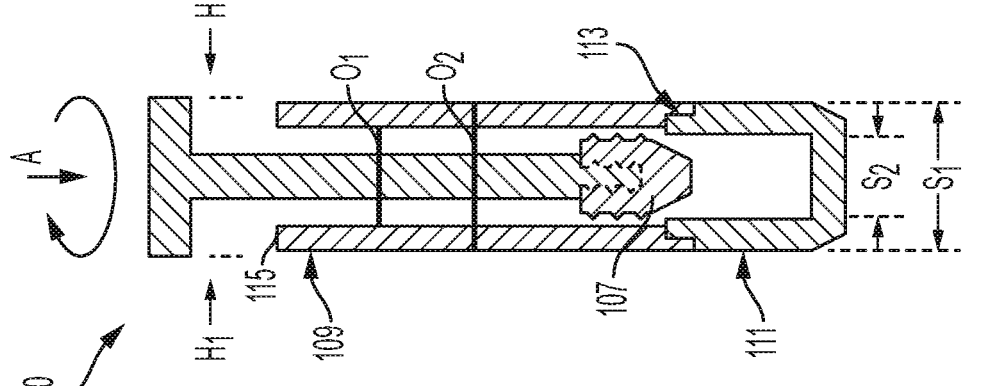
FIG. 1C is a side cross-sectional view of the tendon anchoring assembly of FIG. 1B, showing the screw fully inserted into the sheath.
Figure 1D:
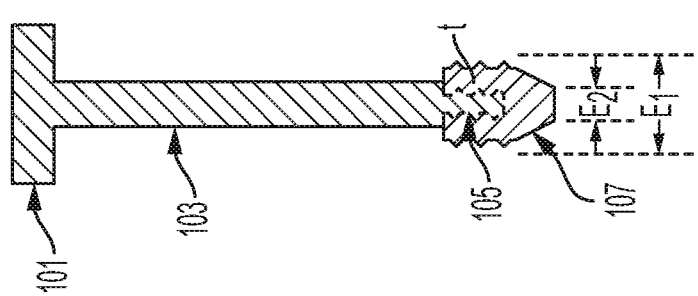
FIG. 1D is a side cross-sectional view of the tendon anchoring assembly of FIG. 1C, showing the inner shaft removed from the screw.

FIGS. 1B-1D illustrate different stages of use of the tendon anchoring system. FIG. 1B illustrates the screw 107 coupled to the inner shaft 103 and being advanced through the outer shaft 109 and toward the sheath 111. As the screw 107 advances into the sheath 111, the inner shaft 103 is rotated, as shown by arrow A, to cause the threads on the screw 107 to threadably engage with internal threads (not shown) formed within the sheath. Clockwise rotation of the inner shaft 103 continues until a distal-face of the handle 101 abuts against the proximal end 115 of the outer shaft 109, as shown in FIG. 1C. At this point, the threaded expander screw 107 is fully threaded into the sheath 111. Abutting of the handle 101 at the proximal end 115 prevents over-insertion of the threaded expander screw 107 into the sheath 111. Thus, the proximal end 115 can function as a hard-stop which indicates full advancement of the screw 107 into the sheath 111. After the threaded expander screw 107 is fully threaded into the sheath 111, the inner shaft 103 can be disengaged from the screw 107 and retracted from the outer shaft 109, as shown in FIG. 1D.

While the handle 101 and the proximal end of the outer shaft 109 can function as a stop to limit insertion of the screw into the sheath, in an exemplary embodiment the drive tip 105 on the inner shaft 103 includes threads formed thereon that mate with corresponding threads formed within the drive recess in the screw 107, as indicated by reference t. When the drive tip 105 is fully threaded into the expander screw 107, further rotation of the inner shaft 103 relative to the expander screw 107 will be prevented. Thus, when the handle 101 on the inner shaft 103 abuts against the proximal end of the outer shaft 109, the threads t will function to prevent further rotation of the inner shaft 103 relative to the outer shaft 109. Without the threaded connection between the drive tip 105 and the drive recess in the expander screw, the inner shaft 103 would be free to rotate, without further distal movement, relative to the outer shaft 109. Such rotation could undesirably cause the expander screw 107 to rotate and advance further distally into the sheath 111.

In another embodiment, the hard-stop 115 of FIG. 1C can have an alternative placement. In particular, FIGS. 2A-2D illustrate another embodiment of the tendon anchoring assembly 200 having a sheath insert tool with an outer shaft 209 and an inner shaft 203 disposed therein and having a drive tip 205 configured to engage a drive recess in a threaded screw 207. As described above, the tip and the drive recess can be threaded for preventing further rotation of the inner shaft 203 relative to the expander screw 207 when the drive tip is fully threaded into the recess. In this embodiment, rather than having a handle on the inner shaft 203 that abuts the proximal end of the outer shaft, the distal end of the inner shaft is configured to abut a proximal end of the sheath to thereby limit the insertion depth.

Figure 2A:
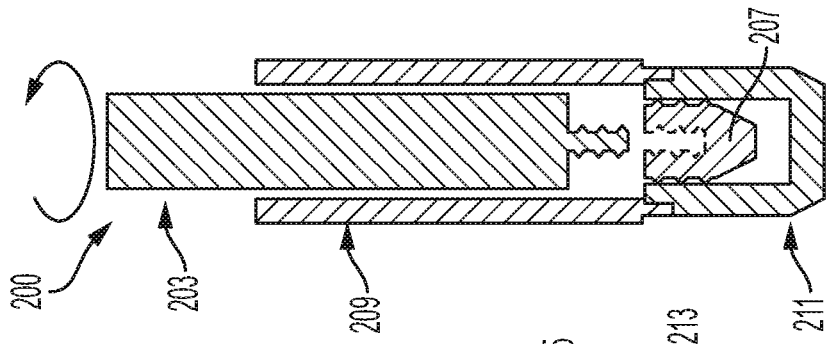
FIG. 2A is a side cross-sectional view of an inner shaft and expander screw of a tendon anchoring assembly according to another embodiment.
Figure 2B:
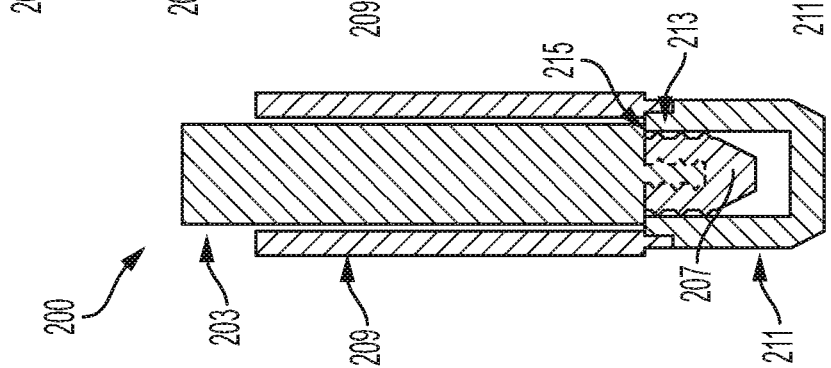
FIG. 2B is a cross-sectional view of the inner shaft and expander screw of FIG. 2A being advanced through an outer shaft and into a sheath coupled to the outer shaft.
Figure 2C:
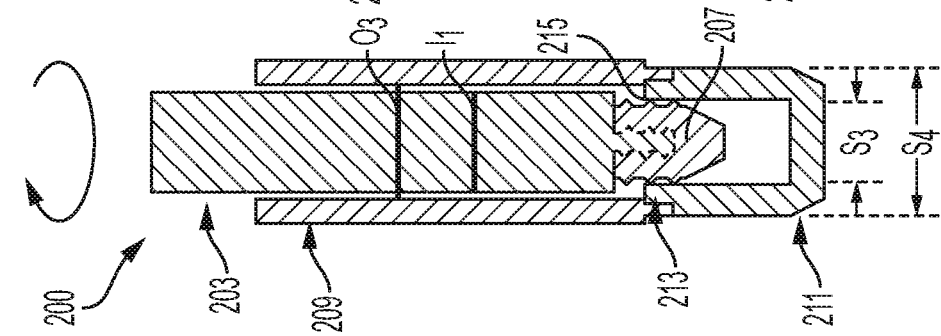
FIG. 2C is a cross-sectional view of the tendon anchoring assembly of FIG. 2B, showing the screw fully inserted into the sheath.
Figure 2D:
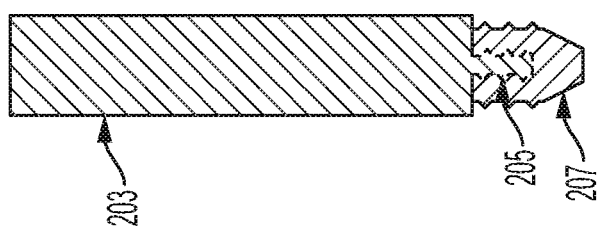
FIG. 2D is a cross-sectional view of the tendon anchoring assembly of FIG. 2C, showing the inner shaft removed from the screw.

As shown in FIG. 2A, the outer shaft 209 has an inner lumen with a diameter $O_3$ that is greater than a diameter $S_3$ of an inner lumen of the sheath 211, but that is less than an outer diameter $S_4$ of the sheath 211. This allows a distal end of the outer shaft 209 to mate to a proximal end 213 of the sheath 211 or at least abuts against it. The inner shaft 203 can have an outer diameter $I_1$ that is greater than a diameter $S_3$ of an inner lumen of the sheath 211 such that the distal end of the inner shaft 203 will abut a proximal end 215 of the sheath 211 to form a hard stop. In use, distal movement of the inner shaft 203 through the outer shaft 209 will advance the expander screw 207 into the sheath 211, as shown in FIG. 2B. Once the expander screw 207 is fully threaded into the sheath 211, as shown in FIG. 2C, the distal end of the inner shaft 203 will abut the proximal end of the sheath 211 to prevent further advance of the inner shaft 203. Since the drive tip 205 on the inner shaft 203 is threaded into the recess in the expander screw 207, further rotation of the inner shaft 203 will be prevented. When desired, the inner shaft 203 can be rotated in a counter-clockwise direction to unthread the drive tip from the drive recess in the expander screw 207, thus allowing the inner shaft 203 to be removed from the outer shaft 209, as shown in FIG. 2D.

Figure 3:
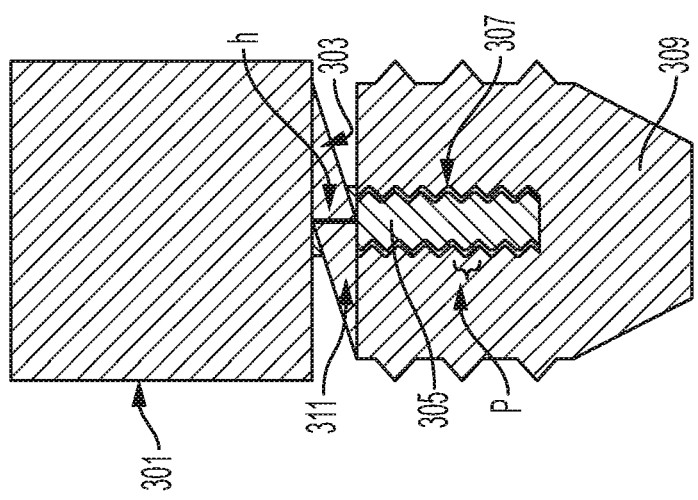
FIG. 3 is a side cross-sectional view of one embodiment of a stop feature formed between a distal end of an inner shaft and an expander screw of a tendon anchoring assembly.

The embodiments in FIGS. 1 and 2 generally describe a tendon anchoring assembly having a distal drive tip which engages a drive recess in the threaded expander screw. The number of turns of the drive tip into the threaded recess in the expander screw determines the tightness. In certain instances, the drive tip may become jammed into the drive recess in the expander screw as a result of overturning of the inner shaft relative to the expander screw. To prevent jamming of the distal drive tip of the inner shaft into the drive recess in the expander screw and to enable repeated unthreading of the inner shaft's drive tip from the expander screw's drive recess, an alternative embodiment of the distal drive assembly is illustrated in FIG. 3. A person skilled in the art will appreciate that the stop feature shown in FIG. 3 can be utilized in connection with the tendon anchoring assemblies of FIGS. 1 and 2.

FIG. 3 illustrates an embodiment of an inner shaft 301 and an expander screw 309 having a feature for limiting an insertion depth of a drive tip 305 on the inner shaft 301 into a drive recess 307 in the expander screw 309. As shown, the expander screw 309 includes a stop surface or wedge 311 formed one a proximal end thereof, and the inner shaft 301 includes a corresponding stop surface or wedge 303 formed on a distal end thereof. Each wedge 303, 311 has a vertical surface that is configured to carry a load and limit over-insertion of the drive tip 305 into the drive recess 307 in the expander screw 309. The wedges 303, 311 can be arranged in opposite directions such that the vertical surfaces are configured to abut one another to thereby prevent further rotation of the inner shaft 301 relative to the expander screw 309. In an exemplary embodiment, the vertical surface on the end of each wedge 303, 311 has a height h that is less than a pitch p of the threads on the drive tip 305 and within the drive recess 307. Such a configuration will allow the wedge 303 on the inner shaft 301 to be spaced apart from the wedge 311 on the expander screw 309 by a distance that is greater than the height h of the vertical surface after one full rotation of the drive tip 305 relative to the drive recess 307. As a result, the wedges 303, 311 will not contact one another during a second rotation of the inner shaft 301 relative to the expander screw 309.

In use, the drive tip 305 will be threaded all the way into the threaded expander screw 309. During the rotation of the inner shaft 301 to thread the expander screw 309 into the sheath, the vertical surface of wedge 303 will strike the vertical surface of wedge 311. Once this occurs, the drive tip 305 is prevented from rotating relative to the drive recess 307, and instead the inner shaft 301 and the expander screw 309 rotate as a unit. Once the expander screw 309 is fully threaded into the sheath, with the stops surfaces described above limiting an insertion depth of the expander screw 309 into the sheath, the inner shaft can be counter-rotated to easily unthread the drive tip 305 from the drive recess 307.

In another embodiment, the drive tip can be a hex drive. FIG. 4 refers to a tendon anchoring procedure in which the drive tip is a hex drive and the rotation of the drive tip is limited by features at a proximal or a distal end of a handle assembly, an inserter tool having an inner and outer shaft, and/or a sheath.

FIGS. 4A-4C illustrates another embodiment of a tendon anchoring system that is similar to the system of FIGS. 2A-2D, and that generally includes an inner shaft 403, an outer shaft 408, an expander screw 407, and a sheath 411. The inner shaft 403 includes a distal drive tip 405 that engages a drive recess in the expander screw 407, as well as a handle 401 coupled to a proximal end thereof. In this embodiment, the drive tip 405 is not threaded, but has a hexagonal or other non-circular shape that engages a complementary drive recess in the expander screw 407. Moreover, the device has a clutch assembly formed between the handle 401 of the inner shaft 403 and the outer shaft 409 to limit rotation of the inner shaft 403 relative to the outer shaft 409. In particular, the distal facing surface of the handle 401 and the proximal facing surface of the outer shaft 409 each include surface features or clutches 421, 423 formed thereon. The clutches can have a variety of configurations, and can be in the form of teeth, protrusions, etc. In use, during the advancement of the inner shaft 403 to thread the screw 407 into the sheath 411, the clutch 421 on the handle 401 will interlock with the clutch 423 on the proximal end of the outer shaft 409 of the sheath inserter tool 400 thereby preventing further rotation. FIGS. 4B-4C illustrate the inner shaft 403 advancing the expander screw 407 into the sheath 411 and once fully threaded into the sheath, the clutches 421, 423 will abut and engage one another to prevent further rotation of the inner shaft 403 relative to the outer shaft 409.

The particular location of clutches 421, 423 can vary. In another embodiment, a clutch can be positioned on a distal end 421a of the inner shaft 403, and a corresponding clutch can be positioned on a proximal end 423a of the sheath 411.

Figure 4E:
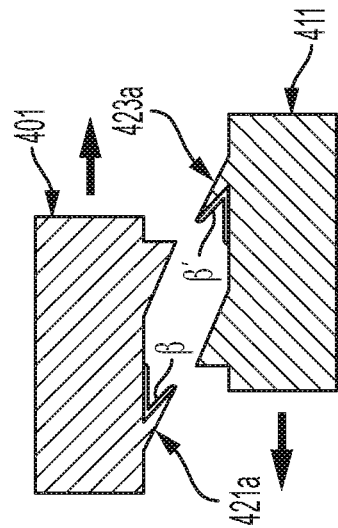
FIG. 4E is a side cross-sectional view showing an alternative configuration of interlocking clutch feature of FIG. 4D.
Figure 4D:
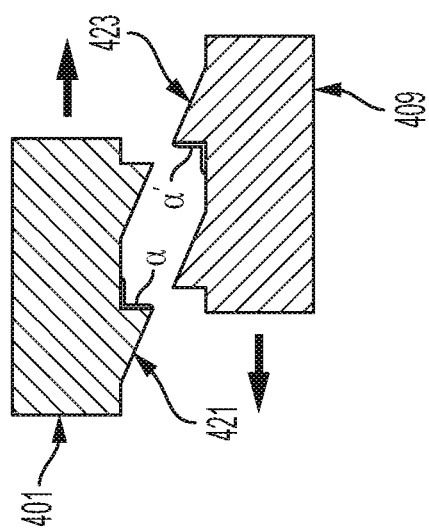
FIG. 4D is a side cross-sectional view showing an interlocking clutch feature formed between the distal end of the inner shaft and the proximal end of the expander screw of FIGS. 4A-4C.

In addition to placement, the clutches can also have a variety of configurations. In one exemplary embodiment, the clutches are in the form of teeth. Alternatively, the clutch engagement feature can be vertical stop surfaces, protrusions, detents, etc. FIG. 4D illustrates a tooth configuration for clutch 421 having an angle α and clutch 423 having an angle α'. The angles α, α' in FIG. 4D are equal to 90 degrees. In another embodiment, the clutches can be configured to have angles β, β' that are less than 90 degrees, as shown in FIG. 4E. In particular, clutch 421a has an angle β and clutch 423a has an angle β'. Such a configuration can result in a mechanical interlock between the clutches, thereby preventing further rotation of the inner shaft and expander screw relative to the outer shaft and sheath once the expander screw is fully threaded into the sheath.

Figure 5A:
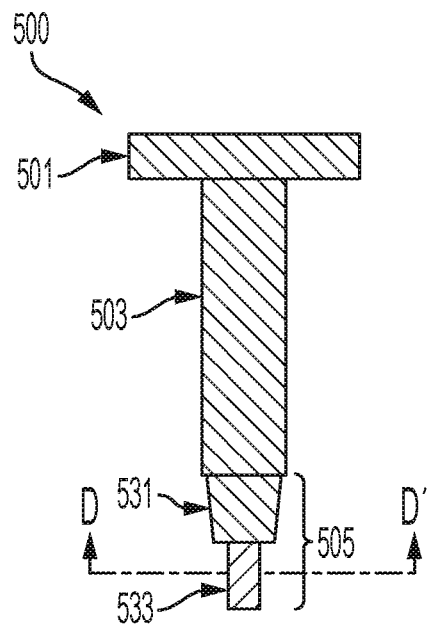
FIG. 5A is a side cross-sectional view of another embodiment of an inner shaft of an inserter tool.

FIGS. 5A-5H illustrate an another embodiment of a tendon anchoring assembly. As shown in FIG. 5A, the inner shaft 503 has a generally elongate configuration with a distal end 505 that is configured to mate to the expander screw 507. The distal end 505 can have a variety of configurations, but in generally it has a proximal drive portion 531 and a distal portion 533. The proximal drive portion 531 is configured to apply a driving force to the expander screw 507 to drive the expander screw into a sheath, and the distal portion 533 is configured to maintain alignment between the inner shaft and the expander screw while also functioning to cause the proximal drive portion 531 to become disengaged from the expander screw 507 with the screw is fully threaded into a sheath. The distal portion 533 can also form a press-fit engagement with the expander screw to hold the expander screw 507 onto the distal end of the inner shaft 503.

Figure 5B:
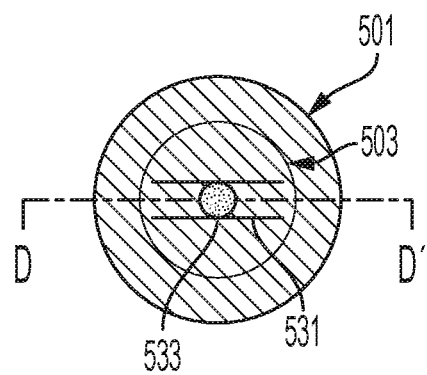
FIG. 5B is a bottom cross-sectional view of the inserter tool of FIG. 5A taken along line D-D'.
Figure 5C:
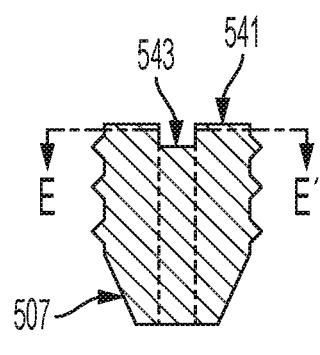
FIG. 5C is a side cross sectional view of one embodiment of an expander screw.
Figure 5D:
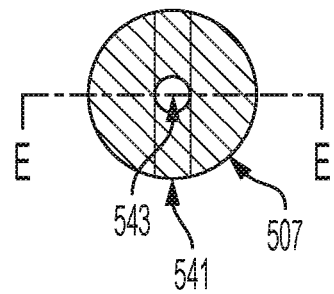
FIG. 5D is a top cross-sectional view of the expander screw of FIG. 5C taken along line E-E'.

As shown in FIGS. 5A and 5B, in the illustrated embodiment the proximal drive portion 531 is in the form of a flat-head driver. A person skilled in the art will appreciate that the proximal drive portion can have any shape that is configured to engage and rotate a drive recess. For example, the proximal drive portion can be square, hexagonal, etc. The illustrated flat-head proximal drive portion 531 is configured to engage a corresponding elongate slot 541 extending across a proximal end of the expander screw 507, as shown in FIGS. 5C and 5D. The distal portion 533 is in the form of a central pin that is configured to extend into an elongate bore 543 formed in the expander screw 507. The central pin is preferably freely rotatable within the elongate bore 543 such that rotation of the pin does not cause any corresponding rotation of the expander screw 507. In an exemplary embodiment, the flat-head 531 has a height that is less than a height of the central pin 533 extending distally from it.

FIGS. 5E-5H illustrate different stages of use of a tendon anchoring assembly 500, which includes the embodiments shown in FIGS. 5A-5D. Initially, as stated above, the distal end 505 having a flat-head 531 and central pin 533 protruding distally from the flat-head can engage the screw 507. In particular, the central pin 533 of the distal end 505 can frictionally mate with a central drive socket 543 of the screw 507 and the flat-head 531 of the distal end 505 can extend into the slot 541. In addition, the distal end of the outer shaft 509 is mated to the proximal end 513 of the sheath 511. As shown in FIG. 5E, with the screw 507 coupled to the inner shaft 503 of tendon anchoring assembly 500, the first stage of the tendon anchoring procedure is to advance the threaded expander screw 507 into the sheath 511. Specifically, inner shaft 503 is plunged in a distal direction F into a proximal end of the outer shaft 509 toward a distal-most end. As shown in FIG. 5F, the handle 501 will abut the proximal end of the outer shaft 509 when the expander screw 507 is fully threaded into the sheath 511. Further rotation of the inner shaft 503 will continue to rotate the expander screw 507 into the sheath 511. Since the handle 501 prevents the inner shaft 503 from advancing distally, the expander screw 507 will move distally away from the distal end of the inner shaft 503. As a result, as shown in FIG. 5G, the flat-head 531 will become disengaged from the slot 541, thereby preventing the inner shaft 503 from driving the expander screw 507 further into the sheath 511. Accordingly, any additional distal clockwise rotation of the inner shaft 503 will not cause over-insertion of the screw 507 into the sheath 511. At this point, the inner shaft 503 can be removed, as shown in FIG. 5H. It is possible to also configured to device such that the flat-head 531 becomes disengaged from the slot 541 when the screw 507 is slightly proud of the proximal end of the sheath 511, so that the screw is perfectly flush with the sheath when the flat-head 531 is fully disengaged.

A person skilled in the art will appreciate that the biceps tenodesis methods and devices disclosed herein can be used in a variety of surgical procedures to prevent trauma or damage to a tendon being attached to a bone via a bone hole. The present invention also has application in conventional joint repair surgeries.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting an anchor in bone, comprising:
   rotating an inner shaft of an inserter tool relative to an outer shaft of the inserter tool to rotatably drive a threaded expander screw distally into a threaded inner lumen of a sheath coupled to the outer shaft and disposed within a bone hole, the expander screw causing the sheath to expand radially outward to engage bone, and the inner shaft having a vertical stop surface formed on a distal end thereof that engages a corresponding vertical stop surface formed on a proximal end of the expander screw to limit distal advancement of a distal drive tip of the inner shaft into a drive recess of the expander screw to a predetermined insertion depth such that over-insertion of the distal drive tip into the expander screw is prevented, each of the vertical stop surfaces having a height that is less than a thread pitch of the expander screw.

2. The method of claim 1, wherein the vertical stop surfaces form a mechanical interlock when mated to prevent rotation of the inner shaft relative to the outer shaft.

3. The method of claim 1, wherein the inner shaft has at least one engagement feature formed thereon and configured to engage a corresponding engagement feature formed on the outer shaft to limit distal advancement of the expander screw into the sheath to a predetermined insertion depth such that over-insertion of the expander screw into the sheath is prevented, wherein the engagement feature on each of the inner shaft and the outer shaft comprises at least one tooth.

4. The method of claim 3, wherein the at least one tooth can be angled such that the engagement feature on each of the inner shaft and the outer shaft form a mechanical interlock when mated to prevent rotation of the inner shaft relative to the outer shaft.

5. The method of claim 1, wherein the distal drive tip of the inner shaft disengages from the drive recess in the expander screw to limit distal advancement of the expander screw into the sheath to a predetermined insertion depth such that over-insertion of the expander screw into the sheath is prevented.

6. The method of claim 5, wherein the drive recess comprises an elongate slot formed in a proximal end of the expander screw.

7. The method of claim 5, wherein the drive recess is threaded for preventing further rotation of the inner shaft relative to the expander screw when the distal drive tip is fully threaded into the drive recess.

8. The method of claim 1, wherein the inner shaft and the outer shaft include complementary abutting surfaces that are configured to contact one another when the expander screw is fully threaded into the sheath.

9. The method of claim 8, wherein the distal drive tip is configured to disengage from the drive recess when the abutting surfaces contact one another.

10. The method of claim 1, wherein the distal drive tip of the inner shaft is threadably engaged with the expander screw such that the inner shaft is prevented from rotating when the distal drive tip is fully threaded into the expander screw.

11. The method of claim 1, wherein a distal end of the outer shaft is configured to abut a proximal end of the sheath to prevent over-insertion of the expander screw into the sheath.

12. The method of claim 8, wherein the complementary abutting surfaces are each disposed at proximal ends of the inner shaft and the outer shaft.

13. The method of claim 1, wherein the inner shaft includes a handle disposed at a proximal end thereof and having a distal-facing surface, and wherein the distal-facing surface is configured to engage a proximal end of the outer shaft and thereby limit insertion of the expander screw into the sheath.

14. The method of claim 1, wherein, once the vertical stop surface formed on the inner shaft engages the corresponding vertical stop surface formed on the expander screw, the inner shaft and the expander screw rotate in unison relative to the outer shaft such that the expander screw is driven into the threaded inner lumen of the sheath.

* * * * *